US00PP12014P2

(12) United States Plant Patent
Hubbard

(10) Patent No.: US PP12,014 P2
(45) Date of Patent: Jul. 24, 2001

(54) NEMESIA PLANT NAMED 'HUBBIRD'

(76) Inventor: Raymond Hubbard, Hill House Nursery, Landscove, nr. Ashburton, Devon (GB), TQ13 7LY ( * ) Notice: Subject to any disclaimer, the term of this patent is extended or adjusted under 35 U.S.C. 154(b) by 0 days.

(21) Appl. No.: 09/328,640

(22) Filed: Jun. 9, 1999

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Nemesia plant named 'Hubbird', characterized by its mostly upright and slightly spreading plant habit; compact, very freely branching and bushy growth habit; numerous slender and filamentous branches; and numerous lavender blue-colored flowers.

1 Drawing Sheet

BACKGROUND OF THE INVENTION

The present invention relates to a new and distinct cultivar of Nemesia plant, botanically known as *Nemesia foetens venten* and referred to by the cultivar name Hubbird.

The new Nemesia is a product of a planned breeding program conducted by the Inventor in Landscove, Devon, United Kingdom. The objective of the program is to create new compact Nemesia cultivars with bushy growth habit and attractive flower colors.

The new Nemesia originated from a cross by the Inventor of two unidentified selections of *Nemesia foetens venten*. The cultivar Hubbird was discovered and selected by the Inventor as a flowering plant within the progeny of the stated cross in a controlled environment in Landscove, Devon, United Kingdom.

Asexual reproduction of the new Nemesia by terminal cuttings taken in a controlled environment in Landscove, Devon, United Kingdom, has shown that the unique features of this new Nemesia are stable and are reproduced true to type in successive generations.

SUMMARY OF THE INVENTION

The new Nemesia has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Hubbird' and distinguish 'Hubbird' as a new and distinct cultivar:

1. Mostly upright and slightly spreading plant habit.

2. Compact, very freely branching and bushy growth habit; numerous slender and filamentous branches.

3. Numerous lavender blue-colored flowers that are about 1.5 cm in length and 1.3 cm in width.

Compared to plants of the parents, the unidentified selections of *Nemesia foetens venten*, plants of the new Nemesia differ in flower color and are more compact, bushier, less upright, have larger flower heads, and flower longer and more freely.

BRIEF DESCRIPTION OF THE PHOTOGRAPHS

The accompanying colored photographs illustrate the overall appearance of the new Nemesia, showing the colors as true as it is reasonably possible to obtain in colored reproductions of this type.

The photograph at the top of the sheet comprises a top perspective view of a typical potted plant of 'Hubbird'.

The photograph at the bottom of the sheet comprises close-up views of typical flowers and leaves of 'Hubbird'. Flower and foliage colors in the photographs may appear different from the actual colors due to light reflectance.

DETAILED BOTANICAL DESCRIPTION

The following observations, measurements, values, and comparisons describe plants grown in Bonsall, Calif., under outdoor full-sun conditions with day temperatures ranging from 18 to 35° C., night temperatures ranging from 13 to 18° C. Plants were grown in one-gallon containers with three plants per container. Color references are made to The Royal Horticultural Society Colour Chart except where general terms of ordinary dictionary significance are used.

Botanical classification: *Nemesia foetens venten* cultivar Hubbird.

Parentage:

*Male or pollen parent.*—Unidentified selection of *Nemesia foetens venten.*

*Female or seed parent.*—Unidentified selection of *Nemesia foetens venten.*

Propagation:

*Type.*—By cuttings.

*Time to initiate roots.*—Summer: About 10 days at temperatures of 24° C. Winter: About 14 days at temperatures of 24° C.

*Time to develop roots.*—Summer: About 21 days at temperatures of 18° C. Winter: About 30 days at temperatures of 18° C.

*Rooting habit.*—Fine and freely branching.

Plant description:

*General appearance.*—Herbaceous upright and slightly spreading plant; compact and bushy; lavender blue zygomorphic flowers are displayed above and beyond the foliage. Suitable for 12.5 to 25-cm containers and hanging baskets. To produce a finished flowering plant in a 12.5-cm container from rooted cuttings, about 8 to 12 weeks are required depending on temperature and light level.

*Plant height.*—About 26 cm from soil level to top of flowers.

*Plant diameter or spread.*—About 24 cm.

*Growth rate/vigor.*—Moderately vigorous.

*Stem description.*—Branching: Very freely branching, typically about 15 laterals; numerous secondary laterals will develop after pinching. Lateral branch appearance: Slender and filamentous. Lateral branch length: Primary laterals, about 10 cm; secondary laterals, about 15 cm. Lateral branch diameter: About 3 mm. Internode length: About 1.5 to 3.5 cm. Texture: Glabrous. Color: 144A.

*Foliage description.*—Arrangement: Opposite, single. Quantity: About 22 per lateral branch. Shape: Lanceolate. Apex: Acute. Base: Acute. Length, lower leaves: About 3.5 cm. Width, lower leaves: About 1.8 cm. Margin: Very slightly serrate. Texture: Smooth, matte. Petiole length: About 4 mm. Petiole diameter: About 2 mm. Color: Young leaves, upper surface: 146A. Young leaves, lower surface: 146B. Fully expanded leaves, upper surface: 146A. Fully expanded leaves, lower surface: 146B to 146C. Petiole: 146 B.

Flowering description:

*Flowers.*—Zygomorphic solitary flowers arranged on terminal racemes; flowering acropetally. Flowers two-lipped with nectar spur. Flowers open rapidly and continue to develop rapidly lasting for only a few days. Petals drop, however ovary and calyx persistent. Not fragrant.

*Natural flowering season.*—Natural flowering season is spring to fall; flowering continuous during this period.

*Quantity of flowers.*—Very floriferous with typically about 58 open flowers and flower buds per raceme; more than 400 open flowers and flower buds per plant.

*Flower length.*—About 1.5 cm.

*Flower width.*—About 1.3 cm.

*Flower depth.*—About 1.3 cm including nectar spur.

*Flower aspect.*—Upward and outward.

*Flower buds.*—Shape: Flattened with spur. Length: About 6 mm. Diameter: About 4 mm. Color: 76D.

*Petals.*—Arrangement: Four upper petals are fused at base to form an upright lip; single lower lip petal with rounded pale yellow 2-mm protuberance which serves as pollinator nectar guide and landing platform; lower petal tip also with nectar spur. Shape: Rounded. Margin: Entire. Length: Upper lip petals: About 1.2 cm. Lower lip petal: About 8 mm. Width: Upper lip petals: About 1.2 cm. Lower lip petal: About 1 cm. Spur length: About 4 mm. Texture: Smooth, soft; matte. Color: When opening, upper surface: 86A. When opening, lower surface: 90D. Mature, upper surface: 86B to 88C to 88D to 87B; lower lip petal with yellow protuberance, 1B to 1C, at petal base. Flower color fading to 85C to 85D with subsequent development. Mature, lower surface: 85A to slightly more blue, 97B to 97D. Spur color: Close to 85B to 85D.

*Sepals.*—Quantity: Five-parted, star-shaped calyx. Shape: Elliptic; apex, acute. Margin: Entire. Calyx length: About 4 mm. Calyx diameter: About 3 mm. Texture: Very minute hairs. Color: Upper surface: 138B. Lower surface: 138A.

*Pedicel.*—Length: About 8 mm. Strength: Slender, but hold flower upright and outward. Angle: Acute. Color: 138A.

*Androecium.*—Stamen number: Typically four per flower. Anther shape: Ovate. Anther size: Less than 5 mm. Anther color: 1D. Amount of pollen: Scarce. Pollen color: 1D.

*Gynoecium.*—Pistil number: One per flower. Stigma shape: Flattened. Pistil length: About 1 mm. Style color: 155D. Stigma color: 155D. Ovary color: 142C.

Disease resistance: Disease resistance to pathogens common to Nemesia has not been documented.

Seed production: Seed production has not been observed.

It is claimed:

1. A new and distinct cultivar of Nemesia plant named 'Hubbird', as illustrated and described.

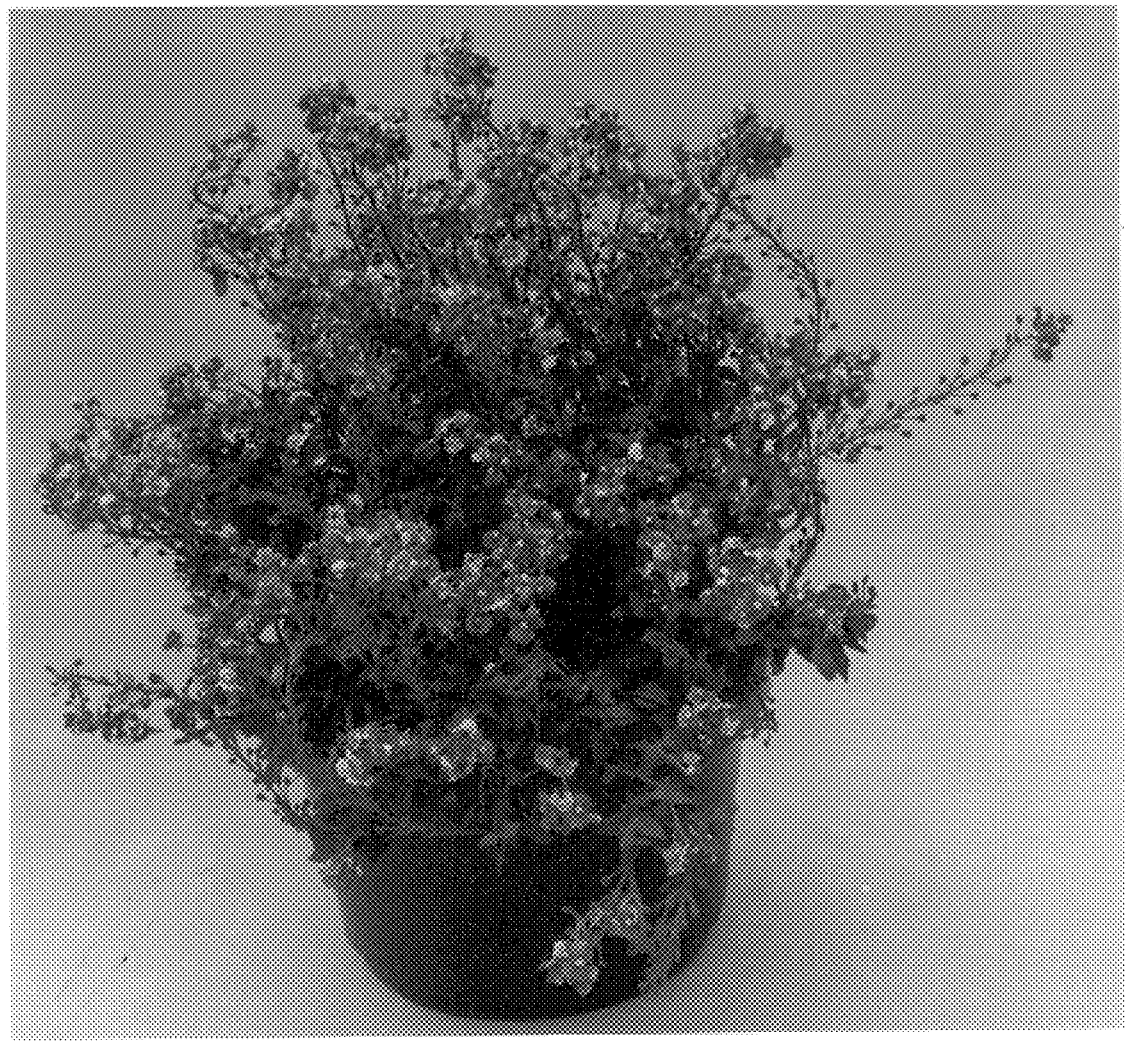
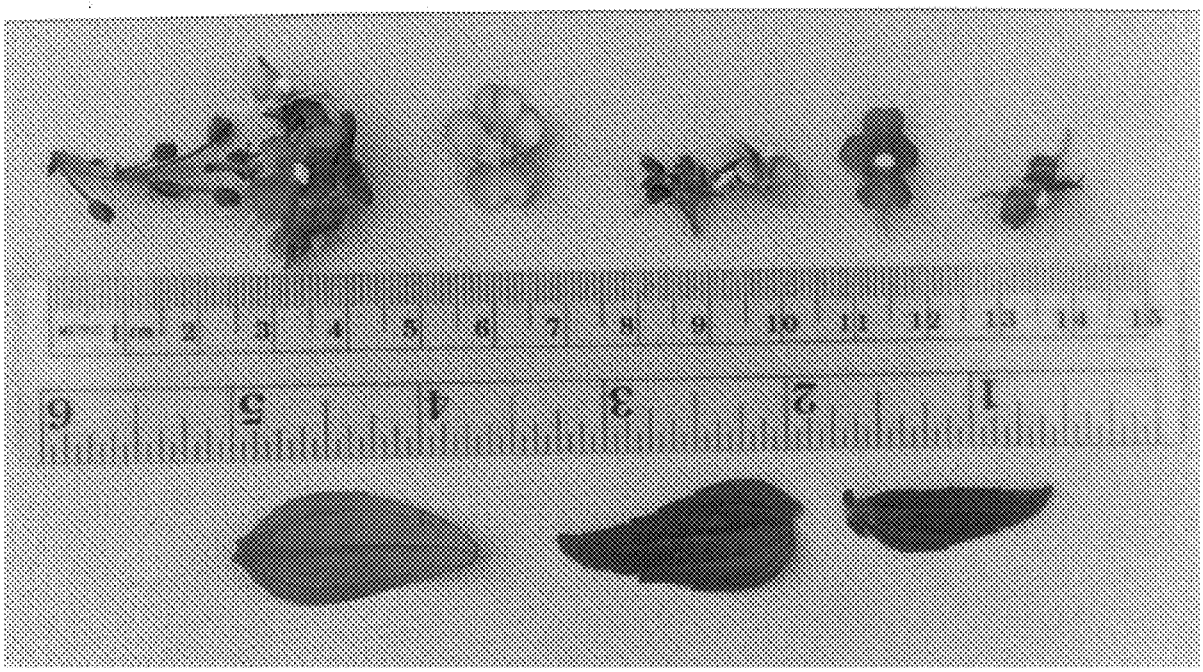

* * * * *